United States Patent [19]
Hill et al.

[11] Patent Number: 6,165,164
[45] Date of Patent: Dec. 26, 2000

[54] CATHETER FOR INJECTING THERAPEUTIC AND DIAGNOSTIC AGENTS

[75] Inventors: Irma P. Hill; Dean M. Ponzi, both of Glendora, Calif.

[73] Assignee: Cordis Corporation, Miami Lakes, Fla.

[21] Appl. No.: 09/280,202

[22] Filed: Mar. 29, 1999

[51] Int. Cl.[7] .................................................. A61M 25/00
[52] U.S. Cl. ............................................ 604/523; 604/95
[58] Field of Search ............................... 604/523, 95, 96; 607/122; 606/41, 42, 45–52

[56] References Cited

U.S. PATENT DOCUMENTS

| | | |
|---|---|---|
| 3,598,119 | 8/1971 | White . |
| 4,578,061 | 3/1986 | Lemelson . |
| 5,244,460 | 9/1993 | Unger et al. . |
| 5,403,311 | 4/1995 | Abele et al. . |
| 5,419,777 | 5/1995 | Hofling . |
| 5,431,168 | 7/1995 | Webster, Jr. . |
| 5,431,649 | 7/1995 | Mulier et al. ............................. 606/41 |
| 5,464,395 | 11/1995 | Faxon et al. . |
| 5,522,815 | 6/1996 | Durgin, Jr. et al. . |
| 5,588,432 | 12/1996 | Crowley . |
| 5,661,133 | 8/1997 | Leiden et al. . |
| 5,725,524 | 3/1998 | Mulier et al. ............................. 606/41 |
| 5,741,320 | 4/1998 | Thornton et al. ....................... 607/122 |
| 5,797,870 | 8/1998 | March et al. . |
| 5,810,804 | 9/1998 | Gough et al. ............................. 606/41 |
| 5,857,997 | 1/1999 | Cimino et al. ............................ 604/95 |
| 5,876,340 | 3/1999 | Tu et al. .................................. 600/439 |
| 5,891,138 | 4/1999 | Tu et al. .................................. 606/41 |
| 5,906,613 | 5/1999 | Mulier et al. ............................. 606/41 |
| 5,921,982 | 7/1999 | Lesh et al. ............................... 606/41 |

FOREIGN PATENT DOCUMENTS

WO 96/41654   12/1996   WIPO .

*Primary Examiner*—Wynn Wood Coggins
*Assistant Examiner*—Kevin C. Sirmons
*Attorney, Agent, or Firm*—Henry W. Collins

[57] ABSTRACT

A steerable injection catheter comprises a catheter body, a deflection control handle, a needle control handle, a tip section, and a means for deflecting the tip section by manipulation of the deflection control handle. A moveable injection needle extends from the needle control handle and through the catheter body and tip section. The needle may be moved out of the distal tip of the catheter by manipulation of the catheter control handle. The catheter also comprises a tip electrode mounted at the distal end of the tip section. An electrode lead wire is electrically connected to the tip electrode. The lead wire extends through a lumen in the tip section, through a lumen in the catheter body and into the deflection control handle. The injection catheter also includes an electromagnetic mapping sensor which is disposed within the distal tip of the catheter for providing tip location information.

18 Claims, 4 Drawing Sheets

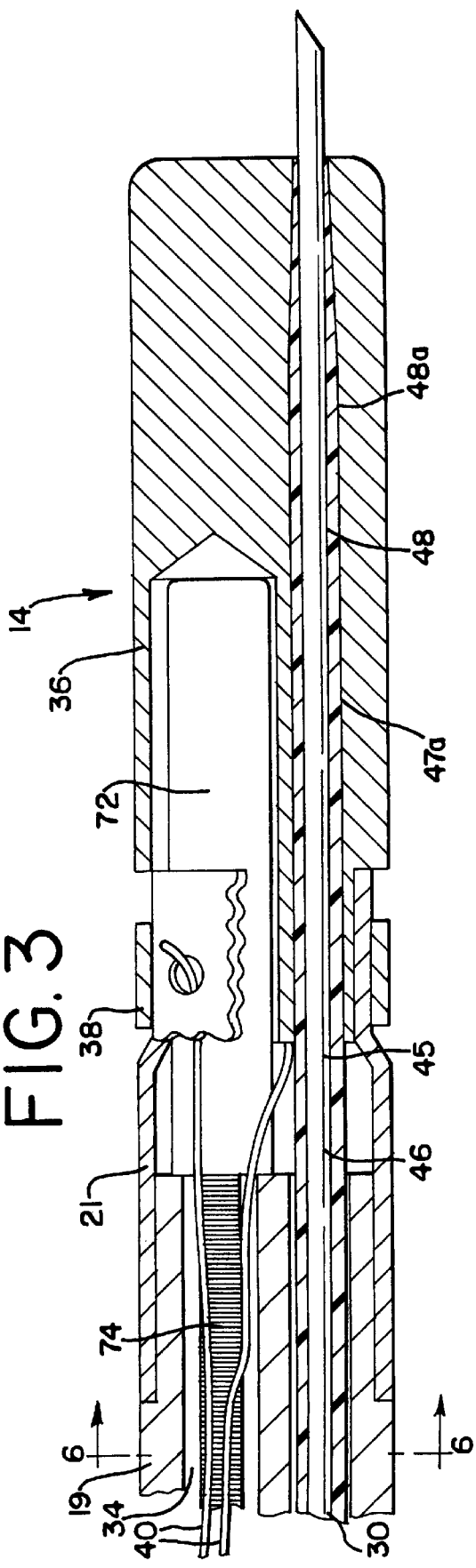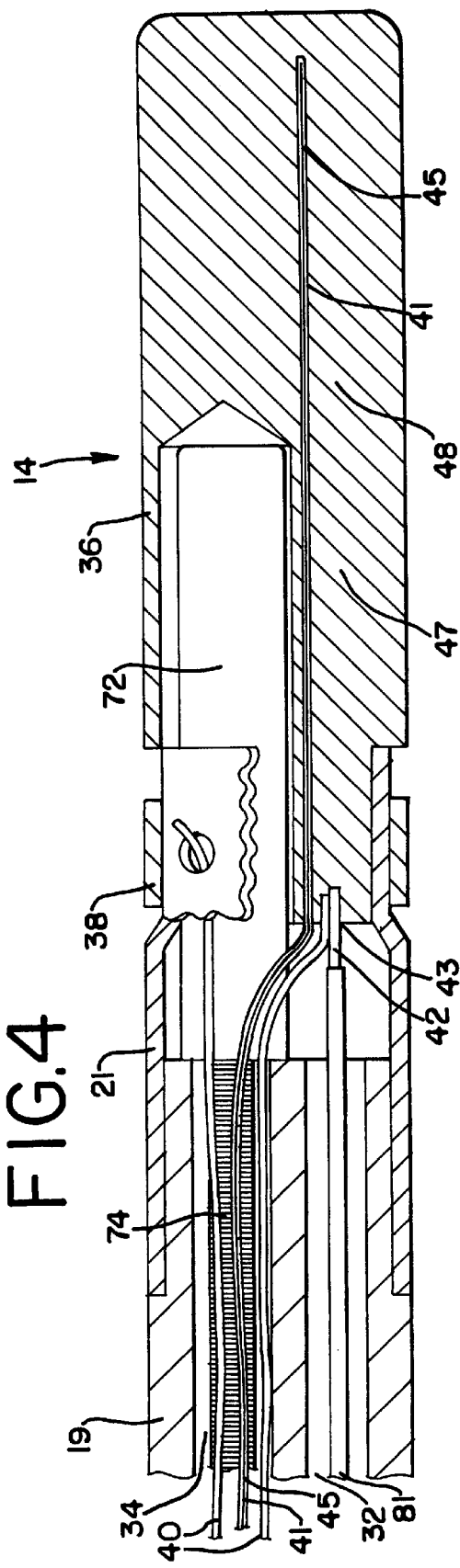

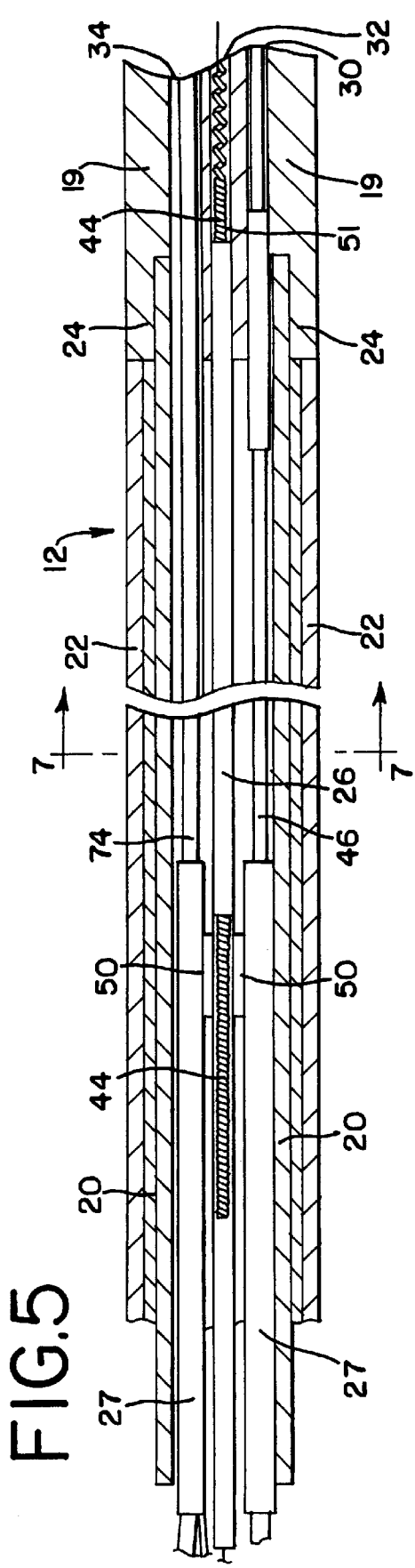
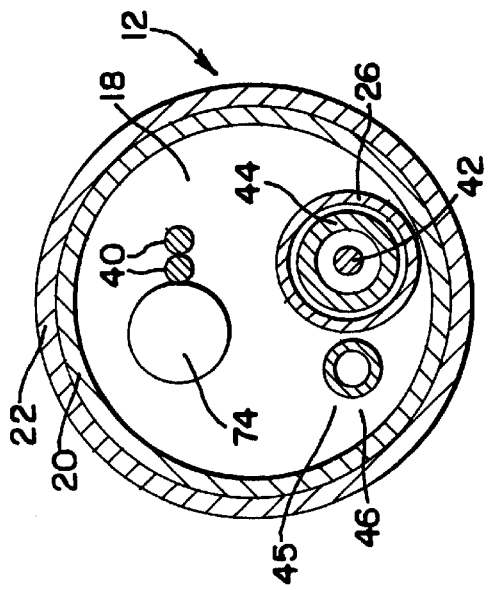
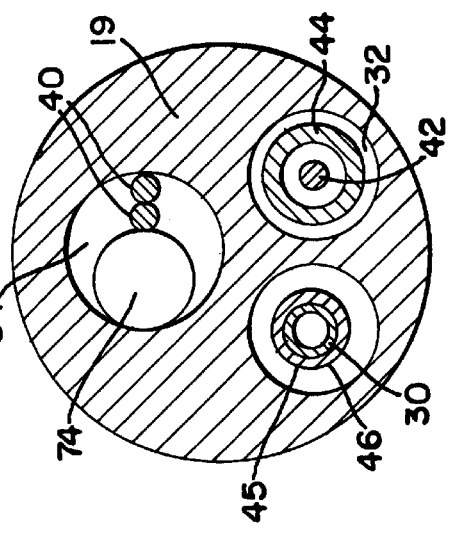

CATHETER FOR INJECTING THERAPEUTIC AND DIAGNOSTIC AGENTS

FIELD OF THE INVENTION

This invention relates to a catheter for infusing therapeutic or diagnostic agents into the tissue of organs, and more particularly to a catheter system in which the infusion needle may be very precisely positioned within the heart to infuse drugs into the wall of the heart.

BACKGROUND OF THE INVENTION

Targeted delivery of therapeutic or diagnostic agents, such as occurs in gene therapy, is very desirable but often presents a difficult challenge. A potential benefit of targeted delivery is that there is an increased efficiency obtained by the precise placement of the therapeutic agent. There are several problems to this procedure which must be overcome in order to obtain satisfactory results from such therapy, such as the problems of obtaining access to the delivery site, transporting the therapeutic agent to the desired site, injecting the therapeutic agent at the proper depth within the organ tissue, steering the distal end of the catheter to a desired location within the organ prior to infusing the agent, and positioning the distal tip of the catheter at precisely the same location where prior measurements have indicated that the drug should be infused. It is also important for a physician to be able to monitor the position of the infusion needle with respect to the wall of the organ. In the case of an organ, such as the heart, in which the walls are in constant motion, the activity of positioning and monitoring the position of the distal tip of the catheter, or infusion needle, becomes especially difficult.

U.S. Pat. No. 3,598,119 discloses a medical device for injecting drugs in which the injection needle is guided through an inner lumen of a catheter for insertion of the needle under skin tissue. A bladder at the distal end of the catheter may be inflated through another lumen for holding the point of the needle point in a fixed position beneath the skin.

U.S. Pat. No. 4,578,061 discloses a catheter for injecting a liquid into a vein, or artery, through an injection needle which is longitudinally movable beyond the distal end of the catheter. A dual chamber system is utilized within the catheter tip to provide for movement of a plunger to extend the injection needle and also to allow for a plunger to be used to apply a predetermined dose of medication through the injection needle.

U.S. Pat. No. 4,578,061 discloses an injection catheter having a longitudinal movable needle which may be moved through a lumen in order to extend out of the side wall of the catheter for injecting a liquid into a blood vessel. The needle is normally retracted into the device so that the needle will not penetrate tissue as the device is moved through a body duct. Thereafter, the needle is moved out of the side of the catheter into a vessel wall in order to infuse a liquid into the wall of a vessel.

U.S. Pat. No. 5,244,460 is directed toward a method for improving blood flow to the heart. More particularly this patent is directed toward a medical procedure for improving the growth of cardiac blood vessels by inserting a catheter into a coronary artery and injecting into the heart a blood vessel growth promoting peptide through an injection port of the catheter.

U.S. Pat. No. 5,419,777 is directed toward a catheter for injection of a fluid into body cavities such as coronary vessels and arteries. This patent, as is the case with the '061 patent, illustrates the use of an injection needle which pretrude laterally through the side walls of the distal tip of the catheter. In the case of drug injections to be made into coronary vessels and arteries, it is very desirable to have the needles extend out of the side walls of the catheter and at an acute angle to the walls of the vessel in order to penetrate the walls of the vessel for injection of the agent.

U.S. Pat. No. 5,431,168, assigned to the same assignee as the present patent application, is directed toward a steerable catheter which includes a puller wire for controlling the distal end of the catheter from a control handle which is mounted on the proximal end of the catheter.

Copending U.S. patent application Ser. No. 09/019,453, entitled "Intracardiac Drug Delivery," assigned to an affiliated company of the assignee of this application, discloses an injection catheter system for infusing a diagnostic or therapeutic agent into the wall of an organ which includes an electromagnetic sensor disposed within the distal tip of the catheter for providing very precise location information for the distal tip of the catheter., The subject matter of this copending patent application is incorporated by reference into the subject patent application.

For obvious reasons, catheters which are used to deliver, therapeutic or diagnostic agents into a targeted region of the heart must be designed so that the physician is able to maintain precise control over the distal tip of the catheter. In addition, the catheter must be designed to provide information as to these precise location of the distal tip, or infusion needle, of the catheter. The present invention is directed toward an improved injection catheter which allows the physician to have greater control over the position of the distal tip and to also obtain accurate information as to the position of the catheter tip.

SUMMARY OF THE INVENTION

The present invention provides for a steerable drug injection catheter system which includes a catheter body having an outer wall, proximal and distal ends, and at least one lumen extending therethrough. The catheter also includes a control handle attached to the proximal end of the catheter for controlling the position of the distal tip of the catheter and for controlling the extension of the injection needle and for the injection of a diagnostic or therapeutic agent. In addition, the catheter includes a tip section which is comprised of a flexible tubing having a lumen extending therethrough, an injection needle which extends through the lumen of the catheter and is movable from a first position in which the distal tip of the needle is withdrawn into the distal face of the tip section to a second position in which the distal tip of the needle extends out of the distal face of the tip section, a needle control means within the control handle for moving the needle from the first position to the second position, and control means for deflecting the distal tip of the catheter upon manipulation of the control handle.

In accordance with another aspect of the present invention, the drug injection catheter also includes a tip electrode mounted at the distal end of the tip section and an electrode conductor which is electrically connected to the tip electrode and extends through the lumen of the tip section and into the control handle. This tip electrode may be used for measuring electrical potentials within the heart, for example cardiac mapping.

In accordance with still another aspect of the present invention, the drug injection catheter includes an electro magnet mapping sensor which is mounted in the distal portion of the tip section for producing electrical signals indicative of the location of the electromagnetic mapping sensor in order to provide very precise information with respect to the location of the distal tip of the catheter.

In accordance with still another aspect of the present invention, the drug injection catheter includes a sensor cable electrically attached to the electromagnetic mapping sensor which extends through the lumen of the catheter and into the control handle where it is then electrically attached to a circuit board situated within the control handle.

In accordance with still another aspect of the present invention, the drug infusion catheter includes a position sensor, preferably an electromagnetic sensor, which is disposed within the distal tip of the catheter for providing precise information as to the location of the distal tip of the catheter.

In accordance with still another aspect of the present invention, the control handle includes a first member fixedly attached to the proximal end of the catheter body and a second member which is movable with respect to the first member. The deflecting means is comprised of a puller wire having a proximal end and a distal end which extends from the control handle through the lumen in the catheter and is fixedly secured within the tip section. The proximal end of the puller wire is fixedly secured to the second member of the control handle whereby manipulation of the first member of the handle relative to the second member of the control handle moves the puller wire relative to the catheter body resulting in deflection of the tip section.

In accordance with still another aspect of the present invention, the deflecting means further comprises a compression coil situation in the catheter body in surrounding relation to the puller wire and extending into the lumen of the tip section in order to prevent buckling of the catheter shaft.

BRIEF DESCRIPTION OF THE DRAWINGS

These and other features and advantages of the present invention will be better understood by reference to the following detailed description when considered in conjunction with the accompanying drawings wherein:

FIG. 3 is a side cross-sectional view of the catheter tip section showing an embodiment having three lumens and showing the position of the electromagnetic mapping sensor and the injection needle;

FIG. 4 is a side cross-sectional view of the catheter tip section showing an embodiment having three lumens and showing the position of the electromagnetic mapping sensor and the puller wire;

FIG. 5 is a side cross-sectional view of the catheter body, including the junction between the catheter body and the tip section;

FIG. 6 is a transverse cross-sectional view of the catheter tip section along line 6—6 showing an embodiment having three lumens;

FIG. 7 is a transverse cross-sectional view of the catheter body along line 7—7; and, FIG. 8 is a side cross-sectional view of the catheter handle;

DESCRIPTION OF A PREFERRED EMBODIMENT

Figure 1:
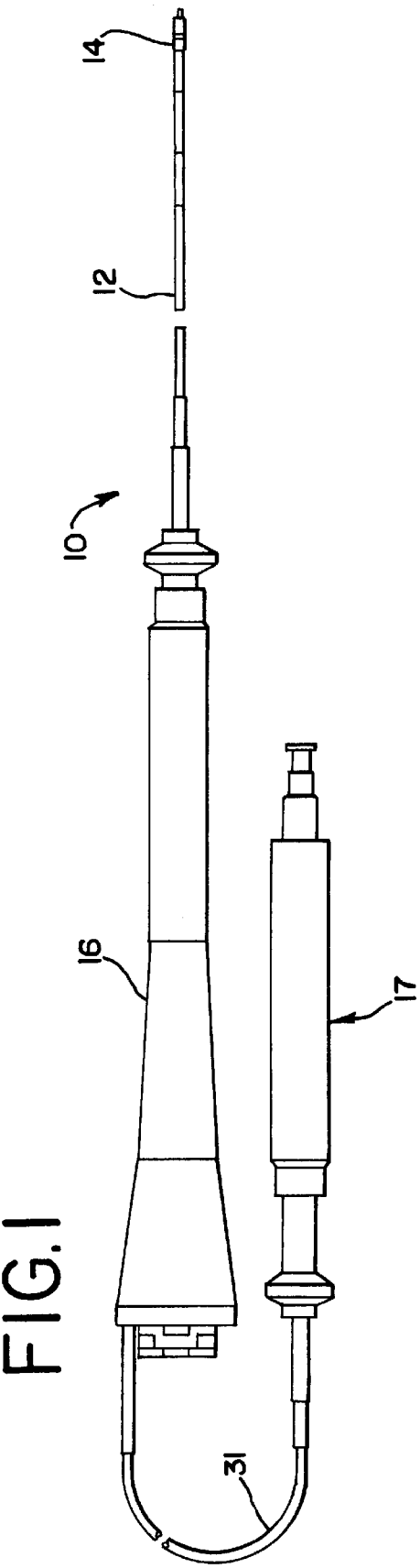
FIG. 1 is a side plan view of one embodiment of the catheter of the present invention.

In a preferred embodiment of the invention, there is provided a catheter for use for injection of a therapeutic or diagnostic agent into the heart. As shown in FIG. 1, catheter 10 is comprised of an elongated catheter body 12 having proximal and distal ends, a tip section 14 at the distal end of the catheter body 12, and a deflection control handle 16 at the proximal end of the catheter body 12 and a needle control handle 17.

Figure 2:
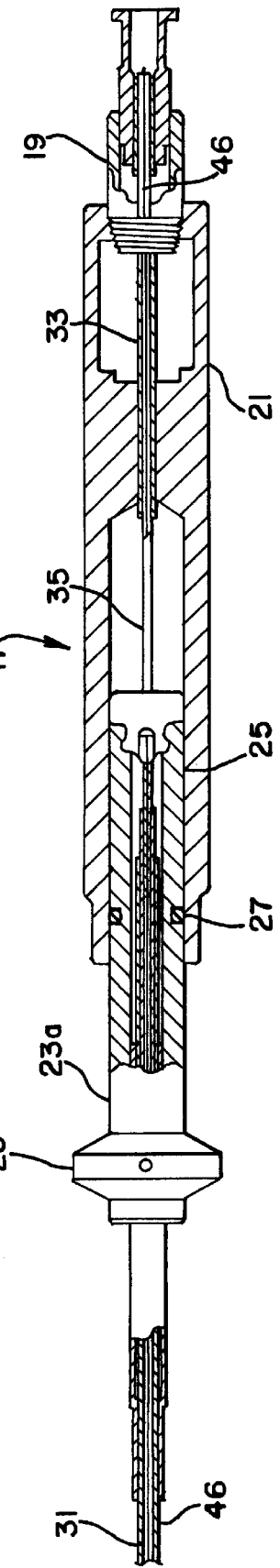
FIG. 2 is a side cross-sectional view of the needle control handle for the embodiment of FIG. 1.
Figure 8:
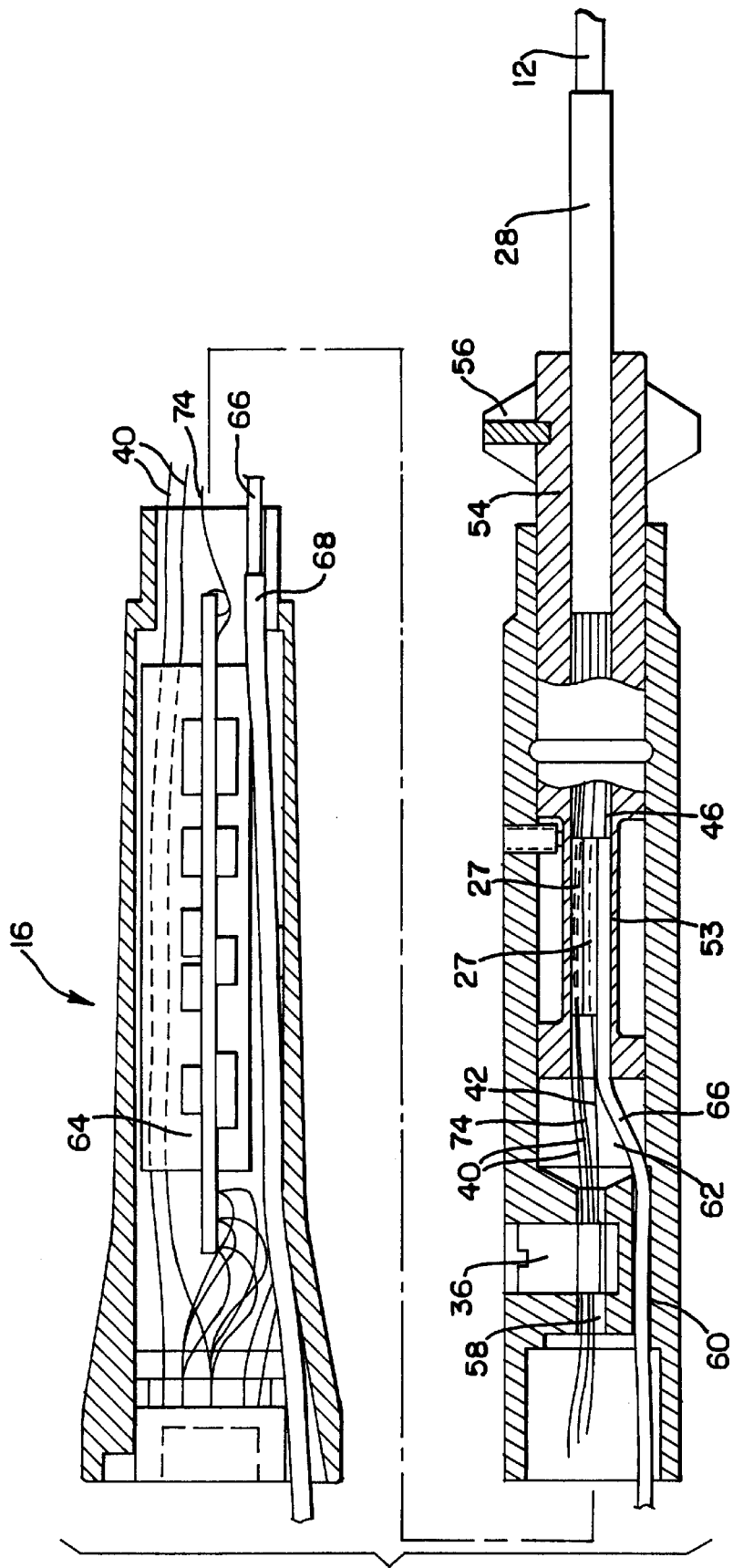

As illustrated in FIG. 2, the needle control handle 17 is comprised of a proximal Luer connector 19 which is threaded into an outer body 21. The control handle also includes a slidable control knob 23 which is attached to a piston 23*a*, which is in turn slidably mounted within a lumen 25 within the outer body 21. A ring seal 27 is disposed between the piston 23*a* and the inner lumen of the outer body 21 to prevent fluid from entering the housing. The slidable control knob 23 and piston 23*a* are fixedly attached to a catheter tubing 31 which extends into the needle control housing 17 and the deflection control housing 16.

In addition, the needle control housing 17 includes a support tube 33 which is fixedly mounted coaxially within the outer body 21 and is preferably formed of stainless steel. Positioned within the lumen of support tube 33 is a slidable tube 35, preferably formed of stainless steel, which is in turn directly coupled to the proximal end of the catheter tubing 31. An injection needle 46 is fixedly attached to an inner lumen of the Luer connector 19 and extends through the lumen of the slidable tube 35 and then through a lumen in the slidable piston 23*a* and then into the catheter tubing 31.

Accordingly, since the injection needle is attached to the Luer connector 19, it may be seen that as the control knob 23 is moved proximally to thereby cause the piston 23*a* to move proximally into the outer body 21 of the needle control housing, the injection needle 46 is caused to slide through the catheter housing 31 with the result that the needle is caused to be extended out of the distal end of the injection catheter system 10. Also, it may be seen that as fluid is applied to the inner lumen of the Luer connector, the fluid is caused to flow through the lumen of the injection needle and to the distal tip of the injection needle 46.

With reference to FIGS. 5 and 7, the catheter body 12 comprises a single, central or axial lumen 18. The catheter body 12 is flexible, i.e., bendable, but substantially non-compressible along its length. The catheter body 12 may be of any suitable construction and made of any suitable material. A presently preferred construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, preferably polyimide. The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is presently preferred because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

A particularly preferred catheter has an outer wall 22 with an outer diameter of about 0.092 inch and an inner diameter of about 0.063 inch and a polyimide stiffening tube having an outer diameter of about 0.0615 inch and an inner diameter of about 0.052 inch.

As shown in FIGS. 3 and 4, the tip section 14 comprises a short section of tubing 19 having three lumens. The tubing 19 is made of a suitable non-toxic material which is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 French. The size of the lumens is not critical. In a particularly preferred embodiment, the tip section has an outer diameter of about 7 French (0.092 inch) and the first lumen 30 and second lumen 32 are generally about the same size, having a diameter of about 0.022 inch, with the third lumen 34 having a slightly larger diameter of about 0.036 inch.

A preferred means for attaching the catheter body 12 to the tip section 14 is illustrated in FIG. 5. The proximal end of the tip section 14 comprises an inner counter bore 24 that receives the outer surface of the polyimide stiffener 20. The tip section 14 and catheter body 12 are attached by glue or the like.

The stiffening tube 20 is held in place relative to the outer wall 22 at the proximal end of the catheter body 12. In a preferred construction of the catheter body 12, a force is applied to the proximal end of the stiffening tube 20 which causes the distal end of the stiffening tube 20 to firmly push against the counter bore 24. While under compression, a first glue joint is made between the stiffening tube 20 and the outer wall 22 by a fast drying glue, e.g. Super Glue®. Thereafter a second glue joint is formed between the proximal ends of the stiffening tube 20 and outer wall 22 using a slower drying but stronger glue, e.g., polyurethane.

Extending through the single lumen 18 of the catheter body 12 are lead wires 40, an injection needle 46, a sensor cable 74, and a compression coil 44 through which a puller wire 42 extends. A single lumen 18 catheter body is preferred over a multi-lumen body because it has been found that the single lumen 18 body permits better tip control when rotating the catheter 10. The single lumen 18 permits the lead wires 40, the injection needle 46, the sensor cable 74, and the puller wire 42 surrounded by the compression coil 44 to float freely within the catheter body. If such wires and cables were restricted within multiple lumens, they tend to build up energy when the handle 16 is rotated, resulting in the catheter body 12 having a tendency to rotate back if, for example, the handle is released, or if bent around a curve, to flip over, either for which are undesirable performance characteristics.

The puller wire 42 is anchored at its proximal end to the control handle 16 and anchored at its distal end to the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

The compression coil 44 extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. For example, when the puller wire 42 has a diameter of about 0.007 inches, the compression coil 44 preferably has an inner diameter of about 0.008 inches. The Teflon® coating on the puller wire 42 allows it to slide freely within the compression coil 44. Along its length, the outer surface of the compression coil 44 is covered by a flexible, non-conductive sheath 26 to prevent contact between the compression coil 44 and any of the lead wires 40, injection needle 46 or sensor cable 74. A non-conductive sheath 26 made of polyimide tubing is presently preferred.

The compression coil 44 is anchored at its proximal end to the proximal end of the stiffening tube 20 in the catheter body 12 by glue and at its distal end to the tip section 14. The glue may be applied by means of a syringe or the like through a hole made between the outer surface of the catheter body 12 and the single lumen 18.

The puller wire 42 extends into the second lumen 32 of the tip section 14. The puller wire 42 is anchored to a tip electrode 36 or to the side of the catheter tip section 14. With reference to FIGS. 4 and 5, within the tip section 14, and distal to the glue joint 51, the turns of the compression coil are expanded longitudinally. Such expanded turns 47 are both bendable and compressible and preferably extend for a length of about 0.5 inch. The puller wire 42 extends through the expanded turns 47 then into a plastic, preferably Teflon®, sheath 81, which prevents the puller 42 from cutting into the wall of the tip section 14 when the tap section 14 is deflected.

With reference to FIGS. 3 and 4, at the distal end of the tip section 14 is a tip electrode 36. Preferably the tip electrode 36 has a diameter about the same as the outer diameter of the tubing 19. The tip electrode 36 is connected to the tubing 19 by means of a plastic housing 21, preferably made of polyetheretherketone (PEEK). The proximal end of the tip electrode 36 is notched circumferentially and fits inside the distal end of the plastic housing 21 and is bonded to the housing 21 by polyurethane glue or the like. The proximal end of the plastic housing 21 is bonded with polyurethane glue or the like to the distal end of the tubing 19 of the tip section 14.

Mounted on the distal end of the plastic housing 21 is a ring electrode 38. The ring electrode 38 is slid over the plastic housing 21 and fixed in place by glue or the like. If desired, additional ring electrodes may be used and can be positioned over the plastic housing 21 or over the flexible tubing 19 of the tip section 14.

The tip electrode 36 and ring electrode 38 are each connected to separate lead wires 40. The lead wires 40 extend through the third lumen 34 of tip section 14, the catheter body 12, and the control handle 16, and terminate at their proximal end in an input jact (not shown) that may be plugged into an appropriate monitor (not shown). If desired, the portion of the lead wires 40 extending through the catheter body 12, control handle 16 and proximal end of the tip section 14 may be enclosed or bundled within a protective tube or sheath.

The lead wires 40 are attached to the tip electrode 36 and ring electrode 38 by any conventional technique. Connection of lead wire 40 to the tip electrode 36 is preferably accomplished by weld 43, as shown in FIG. 4.

The injection needle assembly is comprised of the injection needle 46 which extends from the needle control handle through the body of the catheter, through the distal tip of the catheter and through the tip electrode 36. The injection needle 46 is formed of nitinol, and as illustrated in FIG. 3 is preferably formed with a beveled edge at the distal tip of the needle. Also as illustrated in FIG. 3, the needle is coaxially mounted within a polyimide tube 47a which serves to prevent the needle from buckling and also serves to electrically insulate the needle from the distal electrode 36. The tube 47a additionally serves to provide a fluid-tight seal surrounding the injection needle. The injection needle as shown in FIG. 3 is in a position where the needle extends beyond the distal tip of the electrode as it would be positioned in order to infuse diagnostic or therapeutic fluid into the human heart. The needle is withdrawn within the distal tip of the catheter during the period of time that the catheter is inserted through the vasculature of the body and also during the period of time in which the catheter is removed from the body.

An electromagnetic sensor 72 is contained within the distal end of the tip section 14. The electromagnetic sensor 72 is connected by means of electromagnetic sensor cable 74, which extends through the third lumen 34 of the tip section 14 through the catheter body 12 into the control handle 16. The electromagnetic sensor cable 74 comprises multiple wires encased within a plastic sheath. In the control handle 16, the wires of the sensor cable 74 are connected to a circuit board 64. The circuit board 64 amplifies the signal received from the electromagnetic sensor and transmits it to a computer in a form understandable by the computer. Also, because the catheter is designed for single use only, the circuit board contains an EPROM chip which shuts down the circuit board after the catheter has been used. This prevents the catheter, or at least the electromagnetic sensor, from being used twice. A suitable electromagnetic sensor is described, for example, in U.S. Pat. No. 4,391,199, which is incorporated herein by reference. A preferred electromagnetic mapping sensor 72 is manufactured by Biosense Ltd. Israel and marketed under the trade designation NOGA. To use the electromagnetic sensor 72, the patient is placed in a magnetic field generated, for example, by situating under the patient a pad containing coils for generating a magnetic field. A reference electromagnetic sensor is fixed relative to the patient, e.g., taped to the patient's back, and the injection catheter containing a second electromagnetic sensor is advanced into the patient's heart. Each sensor comprises three small coils which in the magnetic field generate weak electrical signals indicative of their position in the magnetic field. Signals generated by both the fixed reference sensor and the second sensor in the heart are amplified and transmitted to a computer which analyzes the signals and then displays the signals on a monitor. By this method, the precise location of the sensor in the catheter relative to the reference sensor can be ascertained and visually displayed. The sensor can also detect displacement of the catheter that is caused by contraction of the heart muscle.

Using this technology, the physician can visually map a heart chamber. This mapping is done by advancing the catheter tip into a heart chamber until contact is made with the heart wall. This position is recorded and saved. The catheter tip is then moved to another position in contact with the heart wall and again the position is recorded and saved.

The electromagnetic mapping sensor 72 can be used alone or more preferably in combination with the tip electrode 36 and ring electrode 38. By combining the electromagnetic sensor 72 and electrodes 36 and 38, a physician can simultaneously map the contours or shape of the heart chamber, the electrical activity of the heart, and the extent of displacement of the catheter and hence identify the presence and location of the ischemic tissue. Specifically, the electromagnetic mapping sensor 72 is used to monitor the precise location of the tip electrode in the heart and. the extent of catheter displacement. The tip electrode 36 and ring electrode 38 are used to monitor the strength of the electrical signals at that location. Healthy heart tissue is identified by strong electrical signals in combination with strong displacement. Dead or diseased heart tissue is identified by weak electrical signals in combination with dysfunctional displacement, i.e., displacement in a direction opposite that of healthy tissue. Ischemic, or hibernating or stunned, heart tissue is identified by strong electrical signals in combination with impaired displacement. Hence, the combination of the electromagnetic mapping sensor 72 and tip and ring electrodes 36 and 38 is used as a diagnostic catheter to determine whether and where to infuse a drug into the wall of the heart. Once the presence and location of ischemic tissue has been identified, the injection catheter can be deflected so that the needle is normal, i.e., at a right angle, to the ischemic tissue, and the injection needle may then be moved out of the distal end of the catheter and into the wall of the heart.

It is understood that, while it is preferred to include both electrophysiology electrodes and an electromagnetic sensor in the catheter tip, it is not necessary to include both. For example, an injection catheter having an electromagnetic sensor but no electrophysiology electrodes may be used in combination with a separate mapping catheter system. A preferred mapping system includes a catheter comprising multiple electrodes and an electromagnetic sensor, such as the NOGA-STAR catheter marketed by Cordis Webster, Inc., and means for monitoring and displaying the signals received from the electrodes and electromagnetic sensor, such as the Biosense-NOGA system, also marketed by Cordis Webster, Inc.

The electrode lead wires 40, injection needle 46 and electromagnetic sensor cable 74 must be allowed some longitudinal movement within the catheter body so that they do not break when the tip section 14 is deflected. To provide for such lengthwise movement, there are provided tunnels through the glue joint 50, which fixes the proximal end of the compression coil 44 inside the catheter body 12. The tunnels are formed by transfer tubes 27, preferably made of short segments of polyimide tubing. In the embodiment shown in FIG. 5, there are two transfer tubes 27 for the glue joint 50. Each transfer tube is approximately 60 mm long and has an outer diameter of about 0.021 inch and an inner diameter of about 0.019 inch. Extending through one transfer tube 27 are the lead wires 40 and the electromagnetic sensor cable 74. Extending through the other transfer tube 27 is the injection needle 46.

An additional transfer tube 29 is located at the joint between the tip section 14 and the catheter body 12. Extending through this transfer tube is the injection needle 46. This transfer tube 29 provides a tunnel through the glue joint formed when the tip section 14 is glued to the catheter body 12. It is understood that the number of transfer tubes may vary as desired.

Longitudinal movement of the puller wire 42 relative to the catheter body 12, which results in deflection of the tip section. 12, is accomplished by suitable manipulation of the control handle 16. The distal end of the control handle 16 comprises a piston 54 25 with a thumb control 56 for manipulating the puller wire 42. The proximal end of the catheter body 12 is connected to the piston 54 by means of a shrink sleeve 28.

The puller wire 42, lead wires 40 and electromagnetic sensor cable 74 extend through the piston 54. The puller wire 42 is anchored to an anchor pin 36, located proximal to the piston 54. The lead wires 40 and electromagnetic sensor cable 74 extend through a first tunnel 58, located near the side of the control handle 16. The electromagnetic sensor cable 74 connects to the circuit board 64 in the proximal end of the control handle 16. Wires 80 connect the circuit board 64 to a computer and imaging monitor (not shown).

Within the piston 54, the puller wire 42 is situated within a transfer tube 27, and the electromagnetic sensor cable 74 and lead wires 40 are situated within another transfer tube 27 to allow longitudinal movement of the wires and cable near the glue joint 53. The guide tube 66 extends through a second tunnel 60 situated near the side of the control handle 16 opposite the anchor pin 36.

In another preferred embodiment constructed in accordance with the present invention, two or more puller wires (not shown) are provided to enhance the ability to manipulate the tip section. In such an embodiment, a second puller wire and a surrounding second compression coil extend through the catheter body and into separate off-axis lumens in the tip section. The lumens of the tip section receiving the puller wires may be in adjacent quadrants. The first puller wire is preferably anchored proximal to the anchor location of the second puller wire. The second puller wire may be anchored to the tip electrode or may be anchored to the wall of the tip section adjacent the distal end of tip section.

The distance between the distal end of the compression coils and the anchor sites of each puller wire in the tip section determines the curvature of the tip section 14 in the direction of the puller wires. For example, an arrangement wherein the two puller wires are anchored at different distances from the distal ends of the compression coils allows a long reach curve in a first plane and a short reach curve in a plane 90° from the first, i.e., a first curve in one plane generally along the axis of the tip section before it is deflected and a second curve distal to the first curve in a plane transverse, and preferably normal to the first plane. The high torque characteristic of the catheter tip section 12 reduces the tendency for the deflection in one direction to deform the deflection in the other direction.

As an alternative to the above described embodiment, the puller wires (not shown) may extend into diametrically opposed off-axis lumens in the tip section. In such an embodiment, each of the puller wires may be anchored at the same location along the length of the tip section, in which case the curvatures of the tip section in opposing directions are the same and the tip section can be made to deflect in either direction without rotation of the catheter body.

The preceding description has been presented with reference to presently preferred embodiments of the invention. Workers skilled in the art and technology to which this invention pertains will appreciate that alterations and changes in the described structure may be practiced without meaningful departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

That which is claimed is:

1. A steerable cardiac drug injection catheter comprising:
   a catheter body having an outer wall, proximal and distal ends, and at least one lumen extending therethrough;
   a control handle fixedly attached to the proximal end of the catheter body;
   a tip section comprising flexible tubing having proximal and distal ends and at least one lumen extending therethrough, the proximal end of the tip section being fixedly attached to the distal end of the catheter body;
   a tip electrode mounted at the distal end of the tip section, said tip electrode having a distal face and a lumen therethrough;
   an electrode conductor electrically connected to the tip electrode, said conductor extending through the lumen in the tip section, through the lumen in the catheter body and into the control handle;
   an injection needle which is straight and smooth over its entire length extends through the lumen in the catheter body and the lumen in the tip section and extends in fluid tight engagement through the lumen of the tip electrode, said needle being slidable from a first position in which the needle is withdrawn into the tip electrode to a second position in which the needle extends out of the distal face of the tip electrode;
   a slidable needle control knob mounted on the control handle and connected to the proximal end of the injection needle for sliding the injection needle from the first position to the second position; and,
   a deflection control mounted on the control handle for deflecting the catheter upon manipulation of the deflection control.

2. An injection catheter according to claim 1, further comprising an electromagnetic mapping sensor disposed in the tip section for producing electrical signals indicative of the position of the electromagnetic mapping sensor relative to the position of a reference electrode sensor.

3. An injection catheter according to claim 2, further comprising a sensor cable electrically attached to the electromagnetic mapping sensor and extending through the lumen in the tip section, through the lumen in the catheter body and into the control handle, and the sensor cable is electrically attached to a circuit board situated within the control handle.

4. An injection catheter according to claim 3, wherein the control handle comprises a first member fixedly attached to the proximal end of the catheter body and a second member that is movable relative to the first member.

5. An injection catheter according to claim 4, wherein the deflecting means comprises a puller wire having a proximal end and a distal end, the puller wire extending from the control handle, through the lumen in the catheter body and is fixedly secured within the tip section, and the proximal end of the puller wire is fixedly secured to the second member of the control handle, whereby manipulation of the first member of the control handle relative to the second member of the control handle moves the puller wire relative to the catheter body resulting in deflection of the tip section.

6. An injection catheter as defined in claim 5, wherein the first member of the control handle is movable from a first position to a second position relative to the second member of the control handle, and the puller wire is fixedly secured to the second member of the control handle such that when the second member of the control handle is moved from the first position to the second position the puller wire causes the tip section of the catheter to be deflected from a normally straight position to a deflected position.

7. An injection catheter according to claim 6, wherein the deflecting means further comprises a compression coil situated in the catheter body in surrounding relation to the puller wire and extending into the lumen in the tip section.

8. An injection catheter according to claim 7, wherein the compression coil is anchored to the catheter at the proximal end of the catheter body and at the proximal end of the tip section.

9. An injection catheter as defined in claim 1, wherein the outer diameter of the needle is substantially the same as the diameter of the lumen through the tip section to thereby prevent the flow of blood through the lumen of the tip section and the lumen of the catheter body.

10. An injection catheter as defined in claim 9, wherein the needle is formed of an alloy comprised of nickel and titanium.

11. An injection catheter as defined in claim 1, including a sleeve member having a lumen therethrough, said sleeve member is disposed within the lumen of the tip electrode; the needle slidably engages the lumen in the sleeve member; and, the needle is formed of an alloy comprising nickel and titanium.

12. A steerable cardiac drug injection catheter comprising:
a catheter body having an outer wall, proximal and distal ends, and at least one lumen extending therethrough;
a control handle fixedly attached to the proximal end of the catheter body;
a tip section comprising flexible tubing having proximal and distal ends and at least one lumen extending therethrough, the proximal end of the tip section being fixedly attached to the distal end of the catheter body;
an injection needle which is straight and smooth over its entire length extends through the lumen in the catheter body and extending in fluid-tight engagement through the lumen in the tip section, said needle being slidable from a first position in which the needle is withdrawn into the tip section to a second position in which the needle extends out of the tip section;
a slidable needle control knob mounted on the control handle and connected to the proximal end of the injection needle for sliding the injection needle from the first position to the second position; and,
a deflection control mounted on the control handle for deflecting the catheter upon manipulation of the deflection control.

13. An injection catheter as defined in claim 12, wherein the outer diameter of the needle is substantially the same as the diameter of the lumen through the tip section to thereby prevent the flow of blood through the lumen of the tip section and the lumen of the catheter body.

14. An injection catheter as defined in claim 13, wherein the needle is formed of an alloy comprised of nickel and titanium.

15. An injection catheter as defined in claim 13 including a sleeve member having a lumen therethrough, said sleeve member is disposed within the lumen of the tip section; the needle slidably engages the lumen in the sleeve member; and, the needle is formed of an alloy comprising nickel and titanium.

16. A catheter as defined in claim 12, further comprising an electromagnetic mapping sensor in the tip section for producing electrical signals indicative of the location of the electromagnetic mapping sensor.

17. A catheter as defined in claim 16, further comprising a sensor cable electrically attached to the electromagnetic mapping sensor and extending through a lumen in the tip section, through a lumen in the catheter body and into the control handle, wherein the sensor cable is electrically attached to a circuit board situated within the control handle.

18. A catheter as defined in claim 17, wherein the circuit board is electrically attached to a cable, which is electrically attached to a computer for receiving signals from the circuit board.

* * * * *

UNITED STATES PATENT AND TRADEMARK OFFICE
CERTIFICATE OF CORRECTION

PATENT NO : 6,165,164
DATED    : December 26, 2000
INVENTOR(S): Hill et al.

It is certified that error appears in the above-identified patent and that said Letters Patent are hereby corrected as shown below:

[73] Assignee: Cordis Corporation, Miami Lakes, Fla.

should be:

Assignee: Cordis Webster, Inc., Diamond Bar, California

Signed and Sealed this

Fifteenth Day of May, 2001

Attest:

NICHOLAS P. GODICI

*Attesting Officer*   *Acting Director of the United States Patent and Trademark Office*